United States Patent [19]

Crews et al.

[11] Patent Number: 5,560,750
[45] Date of Patent: Oct. 1, 1996

[54] COMPOSITIONS AND METHODS FOR ALTERING THE COLOR OF HAIR

[75] Inventors: Harold R. Crews, Coral Springs, Fla.; Roy M. Evans, Jr.; Joseph O. Rubert, both of Memphis, Tenn.

[73] Assignee: Preemptive Advertising, Inc., Memphis, Tenn.

[21] Appl. No.: 488,257

[22] Filed: Jun. 7, 1995

Related U.S. Application Data

[63] Continuation of Ser. No. 178,464, Jan. 6, 1994, abandoned, which is a continuation of Ser. No. 745,508, Aug. 14, 1991, abandoned, which is a continuation-in-part of Ser. No. 520,637, May 8, 1990, Pat. No. 5,101,841.

[51] Int. Cl.$^6$ ................................. A61K 7/13; D06L 3/00
[52] U.S. Cl. ................... 8/431; 8/406; 8/416; 8/421; 8/424; 8/435; 8/107; 8/110; 8/111; 252/186.21; 252/186.38; 252/186.41
[58] Field of Search ................... 8/405, 406, 416, 8/421, 424, 431, 111, 435, 107, 110; 132/208; 252/186.21, 186.38, 186.41

[56] References Cited

U.S. PATENT DOCUMENTS

| | | | |
|---|---|---|---|
| 2,273,564 | 2/1942 | Dickey et al. | 260/574 |
| 3,231,471 | 1/1966 | Lange | 167/88 |
| 3,893,803 | 7/1975 | Kaiser | 8/10.2 |
| 4,008,043 | 2/1977 | Kalopissis et al. | 8/408 |
| 4,008,999 | 2/1977 | Kalopissis et al. | 8/408 |
| 4,047,888 | 9/1977 | Papantoniou | 8/10.2 |
| 4,054,147 | 10/1977 | Kalopissis et al. | 8/406 |
| 4,150,115 | 4/1979 | Jacquet et al. | 424/70 |
| 4,314,807 | 2/1982 | Grollier et al. | 8/406 |
| 4,363,797 | 12/1982 | Jacquet et al. | 424/70 |
| 4,381,919 | 5/1983 | Jacquet et al. | 8/405 |
| 4,425,132 | 1/1984 | Grollier et al. | 8/405 |
| 4,452,603 | 6/1984 | Konrad et al. | 8/405 |
| 4,473,375 | 9/1984 | Clausen | 8/409 |
| 4,507,280 | 3/1985 | Pohl et al. | 424/70 |
| 4,663,158 | 5/1987 | Wolfram et al. | 8/406 |
| 4,725,282 | 2/1988 | Hoch et al. | 8/408 |
| 4,834,767 | 5/1989 | Helioff et al. | 8/406 |
| 4,840,639 | 6/1989 | Husemeyer et al. | 8/410 |
| 4,900,545 | 2/1990 | Wisotzki et al. | 514/772 |
| 4,947,878 | 8/1990 | Crews et al. | 132/203 |
| 4,957,731 | 9/1990 | Helioff et al. | 8/406 |
| 4,997,451 | 3/1991 | Clausen et al. | 8/421 |
| 5,116,388 | 5/1992 | Brooks | 8/406 |

FOREIGN PATENT DOCUMENTS

| | | |
|---|---|---|
| 0137178 | 4/1985 | European Pat. Off. . |
| 60-028912 | 2/1985 | Japan . |

OTHER PUBLICATIONS

Wall, F. E., "Bleaches, Hair Coloring and Dye Removers" *Cosmetics: Science and Technology*, vol. 2, pp. 279–343 (1972).

*Primary Examiner*—Paul Lieberman
*Assistant Examiner*—Caroline Dusheck
*Attorney, Agent, or Firm*—Synnestvedt & Lechner

[57] ABSTRACT

Disclosed are hair coloring compositions comprising coloring agent and disaccharide. The coloring agent preferably comprises a first oxidizing agent for bleaching the hair, a dyeing agent for adding color to the hair and a second oxidizing agent for developing the dyeing agent. Also disclosed are methods for altering the color of hair to a predetermined degree comprising (a) applying to the hair a hair coloring composition, said composition comprising a coloring agent and a disaccharide; (b) allowing said composition to remain in contact with the hair for a time sufficient to achieve the predetermined degree of color alteration; and (c) substantially removing said composition from the hair.

10 Claims, No Drawings

COMPOSITIONS AND METHODS FOR ALTERING THE COLOR OF HAIR

RELATED APPLICATIONS

The present application is a continuation of U.S. application Ser. No. 08/178,464, filed on Jan. 6, 1994, now abandoned, which is a file wrapper continuation of U.S. application Ser. No. 07/745/508, filed Aug. 14, 1991, now abandoned, which is a continuation-in-part of U.S. application Ser. No. 07/520,637, now U.S. Pat. No. 5,101,841, filed May 8, 1990 which is incorporated herein by reference and which is assigned to the assignee of the present invention. The present application is also related by subject matter to U.S. Pat. No. 4,947,878, issued Aug. 14, 1990 and to patent application Ser. No. 07/745,508 filed Aug. 14, 1991, both of which are incorporated herein by reference and assigned to the assignee of the present invention.

FIELD OF THE INVENTION

The present invention relates to compositions and methods for altering the color of hair. More particularly, the invention relates to bleaching and dyeing compositions containing disaccharides and methods for the application of such compositions to hair.

The treatment of human hair to alter its appearance, including its color and shape, has long been an objective of the hair care industry. In order for such treatments to be considered successful, especially for treatments in vivo, varied and sometimes contradictory requirements must be satisfied. For example, the capability of precisely producing the desired degree of color change is of primary importance for all hair coloring techniques. However, the ability to fully achieve this objective has heretofore been limited by countervailing requirements. For example, hair coloring treatments must be effectively completed in the shortest possible period of time in order to be acceptable to the person undergoing the treatment; yet, longer treatment times have heretofore typically been required to achieve the frequently desired deep tones of color. Moreover, many of the components of the compositions used to alter hair color are known to produce offensive skin and/or scalp irritation, especially when used in concentrations adapted to effect the maximum change in color. From the viewpoint of the hair care professional, it is also highly desirable that the treatment techniques be as simple as possible; yet, one-step methods for dyeing hair have heretofore been rare and/or relatively ineffective.

In general, the color of human hair has heretofore been altered either by bleaching, dyeing or a combination thereof. Mammalian fibers, including human hair, are composed of three major components: a cuticle, a cortex and a medulla. The medulla is central to the hair shaft and is wrapped by strands of keratin, which forms the cortex. The cuticle consists of overlapping flat scales covering the cortex. Melanin is the principal pigment responsible for the color of human hair. Chemical bleaching alters hair coloration by the removal and/or alteration of the melanin. This is typically accomplished by applying oxygen releasing compounds to the hair. Perhaps the most widely used of such compounds is hydrogen peroxide, which is commonly applied in the form of an aqueous solution. Such hydrogen peroxide solutions operate by opening the imbrications of the cuticle, penetrating and attacking the keratin structure and gradually lightening the shade of the hair by oxidizing the melanin. The "lightening" of the hair increases as contact times and hydrogen peroxide concentrations increase. According to prior bleaching methods, however, these conditions also tend to produce scalp irritation and undesirable weakening of the hair shaft. Furthermore, modifying the color of human hair with bleaching agents alone does not necessarily impart the desired color or shade of hair. In particular, bleaching of hair with oxidizing agents alone often results in hair having a "washed out" appearance.

Another method for altering the color of hair involves dyeing the hair. In most hair dyeing techniques, synthetic organic agents are applied to the hair to either temporarily or permanently add color thereto. Examples of temporary or semi-permanent dyes include, for example, azo and nitro compounds, and derivatives of naphthalene and anthraquinone. Semi-permanent dyes are direct dyes and generally do not require any bleaching action to color the hair. However, semi-permanent dyes generally only remain on the hair temporarily and are gradually washed out by successive ordinary shampoos.

Permanent dyes, on the other hand, comprise oxidation dyes, also known in the art as peroxide dyes. Most of these dyes comprise synthetic organic compounds which generally require an amount of hydrogen peroxide or some other non-contaminating compound that readily liberates oxygen for the development of the color on the hair. The compounds frequently referred to as oxidation dyes are more properly referred to as dye intermediates, because their actual dyeing properties are developed only upon oxidation. While a large number of compounds posses the potential for being used as dye intermediates for in vivo hair coloring, only a few such compounds have been used according to prior techniques. For example, many nitro and alkyl compounds posses desirable dyeing properties but have been unavailable for use because they are known to irritate the skin. See Wall, F. E., "Bleaches, Hair Colorings, and Dye Removers," *Cosmetics: Science and Technology*, Vol. 2, 2nd ed., John Wiley & Sons, p. 307 (1972).

Modification of hair color using a dyeing agent alone also frequently produces less than the desired outcome. For example, the prior hair dyeing techniques are known to frequently result in hair having an unnatural "painted" or "brassy" appearance. This undesirable result has previously been overcome by lightening the hair prior to dyeing by exposing the hair to a bleaching operation. However, this complicates and lengthens the coloring procedure.

To avoid this two-step procedure, compositions containing both a bleaching agent and a dyeing agent have been proposed. These compositions generally contain hydrogen peroxide as both the bleach and the developing agent. These bleach-dye combinations suffer from serious drawbacks. In particular, exact proportions of ingredients are usually required such that a precise amount of oxygen is released to ensure that the hair is bleached while the dye is entering it. Furthermore, excessive release of oxygen results in bleaching of the dye itself. See Wall, F. E., "Bleaches, Hair Colorings, and Dye Removers," *Cosmetics: Science and Technology*, Vol. 2, 2nd ed., John Wiley & Sons, pp. 279–343 (1972).

SUMMARY OF THE INVENTION

Accordingly, it is an object of the present invention to provide hair coloring compositions and hair treatment processes which produce desirable color alteration, preferably in relatively short periods of time.

It is a further object of the invention to provide hair coloring compositions which are relatively non-irritating to the skin.

It is a still further object of the invention to provide hair coloring compositions which do not cause unwanted damage to the hair and are readily adaptable for in vivo use.

It is another object of certain embodiments of the invention to provide effective hair coloring processes that provide bleaching and dyeing in a single step.

Applicants have discovered that these and other objects of the present invention are achieved by coloring compositions comprising coloring agent and disaccharide. According to preferred embodiments, the coloring agent comprises a first oxidizing agent for bleaching the hair, a dyeing agent for adding color to the hair and a second oxidizing agent for developing the dyeing agent. Such compositions have been found capable of producing exceptionally deep and desirable color without the need for pre-bleaching. Furthermore, such compositions have surprisingly been found to be effective after only relatively short periods of application while being exceptionally non-irritating to the skin and scalp, and non-damaging to the hair.

Preferred method aspects of the present invention relate to a process for altering the color of hair to a predetermined degree comprising (a) applying to the hair a hair coloring composition, said composition comprising a coloring agent and a disaccharide; (b) allowing said composition to remain in contact with the hair for a time sufficient to achieve the predetermined degree of color alteration; and (c) substantially removing said composition from the hair.

DETAILED DESCRIPTION OF PREFERRED EMBODIMENTS

I. The Compositions

The present coloring compositions comprise two important ingredients: coloring agent and disaccharide. Applicants have found that the inclusion of disaccharide in compositions according to the teachings of the present invention provides the compositions with highly desirable and unexpected properties. In particular, the present compositions have been found to be non-damaging to the hair as compared to prior products. Furthermore, the compositions have also been found to produce exceptionally deep and desirable color after relatively short contact times. According to certain embodiments, this desirable color alteration is achieved without the benefit of a pre-bleaching step.

A. The Coloring Agents

The present compositions comprise coloring agent, preferably a major proportion of coloring agent, and more preferably from about 85 to about 99 percent by weight of coloring agent and more preferably from about 95 to about 99 percent by weight of coloring agent. The term coloring agent is used herein in a non-limiting sense to refer to any agent, compound or composition adapted to alter the color of hair. Thus, the coloring agents of the present invention include those compositions which tend to remove color from the hair as well as those which add color.

It is contemplated that the coloring agents of the present invention will generally include one or more active color compounds and carrier for the active compounds. It will be appreciated that the terms active color compound and carrier are used herein for the purpose of convenience and illustration but not by way of limitation. In particular, the term active color compound refers to those components of the coloring agent which interact chemically or physically with the hair or with other components of the coloring agent to add or remove color from the hair. In contrast, the carrier serves to provide the proper environment for the active compounds and to facilitate, enhance and/or modify delivery and application of the active compounds to the hair. The preferred coloring agents of the present invention comprise from about 5 to about 15 percent by weight of active coloring compounds and from about 85 to about 95 percent by weight of carrier, and even more. preferably from about 10 to about 15 percent by weight of active coloring compound and from about 85 to about 90 percent by weight of carrier.

An important aspect of the present invention resides in the weight ratio of disaccharide to active coloring compounds. Applicants believe that such ratio may vary widely, depending upon numerous factors, such as the type of hair and the degree of color alteration desired. It is preferred, however, that the disaccharide:active coloring compound weight ratio be from about 0.1:1 to about 1:1. Applicants have found that, according to certain embodiments, ratios of less than about 0.1:1 produce compositions which exhibit a decreased ability to protect the hair and skin of the user, while compositions having ratios greater than about 1:1 may exhibit a decreased ability to produce the desired color alteration.

1. Active Compounds

According to certain embodiments of the present invention, the coloring agent comprises an oxidizing agent. As will be appreciated by those skilled in the art, oxidizing agents are commonly used as active components for both removing color from and adding color to hair. As the term is used herein, oxidizing agent refers to those compounds which are oxidizing agents with respect to melanin in the hair or with respect to the dye intermediate used in the oxidative dyeing agents of the present invention. For example, in bleaching operations the oxidizing agent attacks the melanin of the hair and removes color, thereby lightening the hair color. In dyeing operations, an oxidizing agent is typically included to aid in the conversion of the dye intermediates used in permanent dyeing operations. It is seen, therefore, that the amount of oxidizing agent contained in the present compositions will vary widely, depending upon the particular circumstances of each embodiment. It is generally preferred, however, that the present compositions comprise from about 3 to about 20 percent by weight of oxidizing agent. For embodiments in which bleaching and dyeing steps are carried out separately, the compositions preferably comprise from about 10 to about 20 percent by weight of oxidizing agent for bleaching compositions and from about 3 to about 15 percent by weight of oxidizing agent for dyeing compositions. For preferred embodiments in which bleaching and dyeing are carried out using a single composition, the compositions preferably comprise from about 8 to about 14 percent by weight of oxidizing agent and even more preferably from about 8 to about 11 percent by weight of oxidizing agent.

The oxidizing agent to be used in accordance with the present invention may comprise any of a number of conventional or unconventional oxidizing agents. Generally, it is only required that the oxidizing agent be nontoxic, mild in action and free of harmful residue. For the removal of color from the hair, such as in bleaching operations, it is preferred that the oxidizing agent comprise a salt of persulfuric acid ($H_2S_2O_8$), and preferably alkali metal and ammonium salts of persulfuric acid. It is especially preferred for bleaching operations that the oxidizing agent be selected from the group consisting of sodium persulfate ($Na_2S_2O_8$), potassium persulfate ($K_2S_2O_8$), ammonium persulfate (($NH_4)_2S_2O_8$), and mixtures of two or more of the these. Other suitable oxidizing agents for use in bleaching operations, in addition to those exemplified above, will be apparent in view of the present disclosure.

According to other embodiments of the present invention, the hair coloring composition comprises a dyeing agent for adding color to the hair. It is contemplated that the types of dyeing agent suitable for use in accordance with the present invention are numerous and varied, including temporary, semi-permanent and permanent dyes generally known to those skilled in the art. Examples of semi-permanent dyes include, for example, azo and nitro compounds and derivatives of naphthalene and anthraquinone. Such dyeing agents are generally referred to as "non-oxidative" dyeing agents, since these dyeing agents do not require oxidation to color the hair.

It is generally preferred, however, that the dyeing agent of the present invention comprise an oxidative dyeing agent. As the term is used herein, oxidative dyeing agent refers to those dye intermediates or precursors which produce color upon oxidation. The oxidative dyeing agents of the present invention preferably comprise monomeric aromatic compounds which, on oxidation, form oligomers or polymers having extended conjugated systems of electrons in their molecular structure. This oxidative reaction produces oligomers and polymers with electronic structures in the visible spectrum. As a result, oxidation of the dye intermediates or precursors results in the development of color. Especially preferred oxidative dying agents comprise substituted phenols, amino phenols, diamines, including the o-and p-diamines, aminohydroxy compounds of benzene, and derivatives of these which pass through a quinoid stage during oxidation. According to certain embodiments, aromatic amines having two functional groups, such as p-phenylenediamine, are preferred for their ability to yield higher molecular weight colored materials upon oxidative polymerization. Mono functionalized aromatic amines capable of yielding colored conjugated imines, and quinoid dimers, trimers, etc. are preferred according to other embodiments. It is also contemplated that combinations of these various dye precursors may be used.

Suitable oxidative dyeing agents to be used in accordance with the present invention are disclosed, for example, in U.S. Pat. Nos. 4,473,375 and 4,840,639 and F. E. Wall, "Bleaches, Hair Colorings, and Dye Removers," *Cosmetics: Science and Technology*, Vol. 2, pp. 300–320 (1972). These references are incorporated herein by reference. Other dyeing agents to be used in the present invention would be readily apparent to one skilled in the art.

For embodiments comprising an oxidative dyeing agent, its highly preferred that the compositions include an oxidizing agent comprising hydrogen peroxide. It will be appreciated by those skilled in the art that such oxidizing agents operate to develop the color of the dye intermediate and that other developing agents, either alone or in combination with the present oxidizing agents, may be used within the scope of the present invention. What is required in such embodiments is that the developing agent, which is preferably an oxidizing agent, converts the synthetic organic hair coloring intermediates to the desired color.

Applicants have found that the present invention provides a surprising and beneficial result with respect to the amount of oxidizing agent required to develop the color of commonly used oxidative dyeing agents. It has heretofore been common practice to use a 6 wt. % aqueous solution of hydrogen peroxide for developing dye intermediates. Furthermore, it has also been common practice to employ about 2 parts by volume of such hydrogen peroxide solution for every one part by volume of dye base (i.e., dyeing agent plus carrier). In contrast, certain embodiments of the present invention utilize as little as 0.5 parts by volume of hydrogen peroxide solution (6 wt. %) for each part by volume of dye base without any noticeable decrease in hair color alteration. In fact, applicants have discovered that even with this reduced ratio, hair color alteration is effected in substantially shorter time periods than those required by the prior art.

2. The Coloring Agents—Carrier

It will be appreciated by those skilled in the art that many of the active compounds described herein are most readily available in the form of dispersions or solutions of one or more liquids, typically aqueous solutions. It is contemplated the active ingredients of the present invention will frequently be utilized in this from, and accordingly the present compositions preferably include a carrier for the coloring agent. In general it is contemplated that a wide variety of materials will be suitable for use as a carrier, and all such materials are within the scope of the present invention. It is generally preferred that the carrier comprise a liquid, preferably a polar liquid, for facilitating delivery and application of the present coloring agent to the hair. As will be appreciated by those skilled in the art, the physical condition of the carrier may therefore vary widely, ranging, for example, from a thin clear liquid to a creamy paste, depending upon the needs of the particular application.

The carrier of the present invention preferably comprises a solvent for one or more of the active components of the coloring agent. Thus, for compositions containing polar oxidizing agent and/or polar dyeing agents, the carrier preferably comprises a polar liquid, such as water, alcohol and mixtures of these. The term solvent is used in this context in a broad sense to include those liquid components and mixtures of liquid components which have at least some tendency to solubilize at least one active component of the coloring agent. It is especially preferred that the carrier comprise a mixture of water and isopropyl alcohol. The composition preferably comprises solvent in an amount from about 40 to about 65 percent by weight of the composition.

In accordance with a preferred embodiment of the present invention, the carrier comprises a thickening agent for adjusting the rheology of the composition. The type and amount of such thickening agents may vary widely within the scope of the present invention. Thus, the thickening agents suitable for use in the present compositions are those thickening agents typically used in cosmetics and generally include organic and inorganic compounds. Examples of suitable thickening agents include silica, carboxymethylcellulose, fatty alcohols and mixtures of two or more of these. It is preferred that the fatty alcohol comprise lauryl alcohol. A suitable lauryl alcohol is CO-1214, commercially available from Procter & Gamble of Cincinnati, Ohio. A suitable carboxymethylcellulose is CMC-7H3SF, commercially available from Hercules, Inc. of Wilmington, Del. The carrier preferably comprises an amount of the thickening agent to provide the aqueous composition with the desired thickness or viscosity. It is generally preferred, however, that the present coloring composition comprises from about 5 to about 15 percent by weight of thickening agent.

For embodiments in which the composition includes a dyeing agent, and particularly an oxidative dyeing agent, the carrier also preferably comprises an alkalizer for providing the proper environment for the dye intermediate, as is well known in the art. It is especially preferred for such embodiments that the carrier comprise an aqueous solution, and preferably a 28 wt. % solution, of ammonium hydroxide as alkalizer. The amount of alkalizer will of course depend upon the particular dyeing agent. It is generally preferred, however, that the compositions of the present invention include from about 5 to about 10 percent by weight of 28 wt. % aqueous ammonium hydroxide solution.

Embodiments including dyeing agent also preferably include spreading agent to assist in distribution of the dyeing agent evenly along the hair shaft. Suitable spreading agents include most well known surfactants, such as ethoxylated alkylphenols, and preferably octylphenoxy poly(ethyleneoxy)ethanol, which is commercially available as Igepal CA-630 from Rhône-Poulenc/GAF of Wayne, N.J.

The carrier also preferably comprises a detergent for leaving the hair feeling smooth and soft after treatment with the compositions of the present invention. Suitable detergents include those detergents readily known to those skilled in the art, including primary alkyl sulfates of the $C_{12}-C_{18}$ series, salts of oleic acid, ammonium hydroxide, zwitterionic compounds and mixtures of two or more of these. Preferably, the detergent comprises ammonium lauryl sulfate. A suitable ammonium lauryl sulfate is Emersal 633LL$^R$, commercially available from Emery Chemicals Personal Care and Specialties Group of Linden, N.J. Examples of oleic acid and aqueous ammonium hydroxide which are readily available include Emersal 6333LL$^R$, commercially available from Emery Industries, Inc., Fatty and Dibasic Acids Group, Cincinnati, Ohio. An example of a suitable zwitterionic compound to be used in accordance with the present invention is lauramido propyl betaine, commercially available from Mona Industries, Inc. of Patterson, N.J. Other detergents suitable for use in the carrier of the aqueous solution of the present invention would be readily apparent based upon the present disclosure.

In a preferred embodiment of the present invention, the carrier comprises chelating agent. The purpose of the chelating agent in the present compositions is to chelate or bind heavy metals which may be present in the water of the aqueous compositions. In the absence of such chelating agent, such metal ions may deleteriously affect the performance of the active color components. Accordingly, the amount and type of chelating agent will depend, for example, on the quality of the water used in the carrier and the sensitivity of the active color components. Thus, the chelating agent may comprise any of a number of conventional or unconventional chelating agents used in conventional amounts. It is preferred, however, that the chelating agent comprise, and preferably consist of, ethylenediaminetetraacetic acid ("EDTA"). An example of a suitable EDTA to be used in accordance with the present invention is Hamp-ene acid$^R$, commercially available from W. R. Grace and Co. of Nashua, N.H.

For embodiments in which the coloring agent comprises oxidative dyeing agent, it is generally preferred that the carrier include an anti-oxidant to assist in the prevention of premature decomposition of the dye intermediates. It is contemplated that customary types and amounts of anti-oxidants may be used within the scope of the present invention. Sodium sulfite and ascorbic acid are antioxidants which may be used in customary amounts in the compositions of the present invention.

B. The Disaccharide

An important aspect of the present invention is the provision of hair coloring compositions containing disaccharide. In particular, it is contemplated that the disaccharide of the present invention acts as a protecting agent for protecting the keratin fibers of the hair from unfavorable damage and degradation while also permitting, and preferably enhancing, the oxidation of melanin contained in the hair. Furthermore, applicants have found that the presence of disaccharide in hair treatment compositions tends to also protect the scalp of the person being treated and the hands of the hair care professional from irritation and burning. In embodiments in which the composition includes oxidative dyeing agent, the disaccharide appearers to also act as a protecting agent to the extent that it inhibits premature or excessive development of the dye intermediate.

An especially preferred embodiment of the present invention provides coloring compositions in which the coloring agent comprises oxidative dyeing agent and oxidizing agent, the amount and type of the oxidizing agent being effective to develop said oxidative dyeing agent and to remove color from the hair. Such embodiments are preferred for the advantage of providing a composition which is highly effective for substantially simultaneously removing and adding color to hair, a characteristic which has been long sought but not heretofore fully achieved. The difficulty encountered by prior art compositions stemmed from the conflicting and contradictory requirements of the components of such compositions. In particular, bleaching of hair to remove color has heretofore generally required a type and amount of oxidizing agent which has been detrimental to effective performance of the dye intermediates. Thus, it has heretofore been difficult if not impossible to effectively formulate compositions containing a type and amount of oxidizing agent effective to perform both lightening and development functions. Applicants have unexpectedly found that such a characteristic is possessed by certain preferred embodiments of the present compositions.

Without being bound by or limited to any particular theory of operation, it is believed that the ability of the present composition to both lighten hair and develop dye intermediates is due, at least in part, to the beneficial effects of disaccharide in the present compositions. In particular, it is believed that the disaccharide component, and preferably sucrose, favorably regulates development of the dye intermediate, enhances the oxidative reaction of the melanin in the hair, and moderates harmful oxidative attack on the keratin fibers in the hair. In connection with regulation of the reaction of the dye intermediates, it is contemplated that the disaccharide may interfere to a favorable extent with the chemical interaction of the oxidizing agent and the dye intermediate. Furthermore, it is believed that, in the absence of disaccharide, bleaching of hair by exposure to oxidizing agents causes a disadvantageous degradation of the keratin fibers, and that this degradation inhibits binding of the developed dye to the keratin fiber. According the present invention, it is expected that the disaccharide acts to preferentially favor reaction of the oxidizing agent with the melanin while simultaneously protecting the keratin fibers from degradation. Applicants have thus discovered that the inclusion of disaccharide, such as sucrose, in compositions for the coloring of hair imparts several desirable characteristics to such compositions.

As is well known to those skilled in the art, disaccharides are carbohydrates comprised of two monosaccharide units. As used herein, the term disaccharide refers to all known and available disaccharide compounds, including all stereoisomeric and enantiomeric forms thereof. While it is contemplated that all such disaccharides are adaptable for use in the compositions of the present invention, it is highly preferred that the disaccharide comprise, and preferably consist essentially of, a disaccharide which does not contain a "free" aldehyde or ketone group. It is also preferred that the disaccharide of the present invention does not reduce Tollens' or Fehlings' reagent, hereinafter referred to as a "non-reducing disaccharide." Sucrose, which does not contain a free aldehyde or ketone group, is an especially preferred non-reducing disaccharide. Because of its ready availability and low cost, (+)—sucrose is especially preferred for use in connection with the compositions of the present invention.

It is contemplated that the amount of disaccharide used in accordance with the present invention may vary widely, depending upon numerous factors, such as hair type and the desired color alteration. It is generally preferred, however, that the coloring compositions of the present invention comprise from about 1 to about 5 percent by weight of disaccharide, with from about 1 to about 3 percent by weight being more preferred. According to especially preferred embodiments, the coloring compositions comprise about 2 percent by weight of disaccharide.

As mentioned hereinbefore, the ratio of disaccharide to active color compounds is an important aspect of certain embodiments of the present invention. It is generally preferred that such ratio, on a weight basis, is from about 0.1:1 to about 1:1.. For coloring compositions which do not contain oxidative dyeing agents, for example bleaching compositions, the dissaccharide: active coloring compound weight ratio is preferably from about 0.1:1 to about 0.3:1. For coloring compositions which do contain oxidative dyeing agents, the weight ratio of disaccharide: active coloring compound is preferably from about 0.2:1 to about 0.4:1.

II. The Kits

According to certain embodiments of the invention, the present compositions are provided in kit form and preferably comprise a first container containing a first composition for adding color to the hair, a second container containing a second composition comprising carrier components and a third container containing an oxidizing agent. In such embodiments, it is contemplated that disaccharide is preferably included in either the first composition or the second composition or both the first and second compositions. It is contemplated that the hair care professional or in-home user can combine the contents of the kit to produce numerous and varied compositions of the present invention, thereby having the ability to achieve a range of hair coloring effects.

The first container preferably contains a composition comprising dyeing agent, and even more preferably a composition comprising oxidative dyeing agent. For the purpose of convenience, first compositions which contain dyeing agent are sometimes referred to herein as dye base. It is preferred that the first composition of the kit of the present invention is itself a composition according to the present invention. That is, it is preferred that the first composition also contain disaccharide. In such embodiments, the composition in the first container preferably comprises from about 0.2 to about 2.5 percent by weight of oxidative dyeing agent, from about 3 to about 5 percent by weight of disaccharide and about 85 to about 95 percent by weight of carrier.

The second composition, which is also preferably a composition of the present invention comprising carrier components and disaccharide, is sometimes referred to herein as bleach oil. The bleach oil preferably consists essentially of carrier components and disaccharide wherein the amount of disaccharide is preferably from about 3 to 5 percent by weight of the bleach oil. Other ingredients adaptable for use in the present compositions to effect the handling, rheology, etc., as described hereinbefore, may also be included in the composition in the second container.

The third container contains a composition, and preferably a composition in solid powder form, comprising oxidizing agent. The oxidizing agent is preferably selected so as to remove color from the hair. Thus, for the purpose of convenience, the third composition is sometimes referred to herein as bleach booster powder. For example, the composition contained in the third container preferably includes oxidizing agent comprising a salt of persulfuric acid ($H_2S_2O_8$), and preferably alkali metal and ammonium salts of persulfuric acid, such as sodium persulfate ($Na_2S_2O_8$), potassium persulfate ($K_2S_2O_8$), ammonium persulfate (($NH_4)_2S_2O_8$). Other ingredients adaptable for use in the present compositions, as described hereinbefore, may also be included in the composition of the third container.

In operation, the bleach oil is adapted to be combined with a portion of the contents of the first container, or with a portion of the contents of the third container, or with a portion of the contents of both the first and third containers to produce a composition according to the present invention. For example, the oxidizing agent in the third container is especially adapted to remove color from hair when combined with bleach oil described above. Thus, a bleaching composition according to the present invention is prepared by mixing a portion of the first and third containers hereof. Furthermore, the composition in the first container is suitable for use alone or in combination with a peroxide solution to add color to hair. For embodiments in which both removal of color from and addition of color to the hair is desired, portions of the contents of all three containers may be combined.

In all cases, it is contemplated that an aqueous peroxide solution, and preferably a 20 vol solution, which is normally not part of the kit, will preferably be utilized to produce a final composition according to the present invention.

III. The Methods

The present invention provides methods for conveniently coloring hair comprising applying a composition of the present invention to the hair, allowing said composition to remain in contact with the hair for a time sufficient to alter the color of the hair and substantially removing said composition from the hair.

According to especially preferred aspects of the present invention, the methods achieve bleaching and dyeing of hair in a one-step procedure. This method comprises applying to the hair an aqueous hair coloring composition comprising an oxidative dyeing agent, disaccharide, and oxidizing agent, the amount and type of the oxidizing agent being effective to develop said oxidative dyeing agent and to remove color from the hair. Such methods are highly preferred for the ability to achieve effective removal of color from hair and addition of color to hair in a single step. The composition is preferably allowed to remain in contact with the hair for a time sufficient to bleach and dye the hair to the desired degree. The composition is then removed from the hair, preferably by steps which comprise rinsing with water.

The application of the compositions of the present invention to the hair comprises application procedures generally known to those skilled in the art. For example, the hair may be dry upon application of the compositions. Conversely, the hair may be wetted with water prior to the application of the compositions. In either event, the composition is applied in an amount so that it is substantially completely and evenly distributed throughout the hair.

In accordance with the method aspects of the present invention, the composition is allowed to remain in contact with the hair for a period of time effective to color the hair by both bleaching and dyeing the hair. Preferably, the composition is allowed to remain in contact with the hair for about 5 to about 20 minutes. Applicants have found that, due in large part to the beneficial properties of the present compositions, the contact times required by the preferred methods of the present invention to achieve a desired color alteration are substantially shorter than those required by prior art procedures. Accordingly, the color altering compositions of the present invention are preferably allowed to remain in contact with the hair for no more than about 10 minutes, and even more preferably from about 5 to about 10 minutes.

After the color of the hair has been altered to the desired extent, the compositions of the present invention are preferably removed from the hair by rinsing the hair with water. Thereafter, the hair may be cut, styled and dried in any desirable manner.

The invention will now be further described with reference to the following illustrative but non-limiting examples.

EXAMPLE 1A

The composition reported under column A in Table 1 is prepared. In particular, a liquid dye base comprising dye intermediate, carrier and sucrose is prepared in accordance with the composition indicated under the column heading GB in Table 4. The composition described under heading GB in Table 4 consists of about 0.2 parts by weight (PBW) of oxidative dyeing agent, about 95.3 PBW of carrier and about 4.5 PBW of sucrose. The carrier comprises about 15.7 PBW deionized water, about 11.7 PBW of isopropyl alcohol, about 15.5 PBW of alkalizer, about 29.7 PBW of detergent, about 13.5 PBW of thickening agent, about 9 PBW of spreading agent, about 0.6 PBW of anti-oxidant and about 0.2 PBW of chelating agent. The alkalizer consists of a 28 weight percent aqueous solution of ammonium hydroxide. The detergent consists of about 16.2 PBW of oleic acid (Emersal 6333LL) and about 13.5 PBW of Monoteric LMAB. The thickening agent consists of about 13.5 PBW of lauryl alcohol and the spreading agent consists of about 9 PBW of the surfactant octylphenoxypoly(ethyleneoxy)ethanol (Igepal CA-630). The anti-oxidant consists of about 0.4 PBW of sodium sulphite and about 0.2 PBW of isoascorbic acid. The chelating agent consists of about 0.2 PBW of EDTA (Hamp-ene). The dye intermediate GB is described under the heading GB in Table 5.

A bleach booster powder consisting of about 36 PBW of potassium persulfate, about 21 PBW of ammonium persulfate, about 36 PBW silica thickening agent, about 5 PBW of carboxymethylcellulose (CMC-7H3SF), about 1 PBW of fumed silica (CAB-O-SIL M5), and about 1 PBW of chelating agent (Hamp-ene acid) is prepared.

A developer (oxidizing agent) for the dye intermediate GB comprising a 6 percent by weight solution of hydrogen peroxide is provided. The developer thus comprises about 6 PBW of active coloring compound and about 94 PBW of carrier.

A coloring composition according to the present invention is prepared just prior to use by combining about 100 PBW of the dye base with about 30 PBW of the bleach booster powder and about 200 PBW of the developer. The coloring composition thus produced is described under column heading A in Table 1.

The coloring composition is applied to the hair of a human female subject having level two brown color hair by working it into a rich lather on the head of the female subject. After working the composition into the hair for about 3–5 minutes so as to ensure uniform application of the composition evenly to all of the hair of the subject, the composition is allowed to remain on the hair an additional 10 minutes. The hair of the subject is then rinsed thoroughly with water and allowed to dry. It is observed that the hair of the subject is altered from a level two brown to a level twelve blonde. Rich, deep tones are produced, and a brassy appearance is avoided. The hair is observed to be relatively undamaged by the treatment, and no irritation of the scalp of the subject or the skin of the hair professional is reported.

EXAMPLE 1B

Example 1A is repeated except that the final coloring composition is prepared just prior to use by combining about 100 PBW of the dye base with about 30 PBW of the bleaching powder and about 100 PBW of the developer. The coloring composition thus produced is described under column heading B in Table 1.

The coloring composition is applied to the hair of a human female subject having level two color hair by working it into a rich lather on the head of the female subject. After working the composition into the hair for about 3–5 minutes so as to ensure uniform application of the composition evenly to all of the hair of the subject, the composition is allowed to remain on the hair an additional 10–15 minutes. The hair of the subject is then rinsed thoroughly with water and allowed to dry. It is observed that the hair of the subject is altered from a level two 2 to level twelve ash blonde. Rich, deep tones are produced, and a brassy appearance is avoided. The hair is observed to be relatively undamaged by the treatment, and no irritation of the scalp of the subject or the skin of the hair professional is reported.

A comparison of Example 1A and 1B reveals that the beneficial attributes of the present invention remain substantially undiminished even when the ratio of developer to dye base is substantially reduced. That is, the amount of developer used in Example 1B is only about one half of the amount of developer which is used in Example 1A. Despite this substantial reduction in developer, the result is observed to be substantially unchanged.

EXAMPLE 1C

Example 1A is repeated except that the final coloring composition is prepared just prior to use by combining about 100 PBW of the dye base with about 30 PBW of the bleaching powder and about 50 PBW of the developer. The coloring composition thus produced is described under column heading C in Table 1.

The coloring composition is applied to the hair of a human female subject having level two color hair by working it into a rich lather on the head of the female subject. After working the composition into the hair for about 3–5 minutes so as to ensure uniform application of the composition evenly to all of the hair of the subject, the composition is allowed to remain on the hair an additional 5–8 minutes. The hair of the subject is then rinsed thoroughly with water and allowed to dry. It is observed that the hair of the subject is altered from a level two to level six. Rich, deep tones are produced, and a brassy appearance is avoided. The hair is observed to be relatively undamaged by the treatment, and no irritation of the scalp of the subject or the skin of the hair professional is reported.

A comparison of Examples 1A and 1C further illustrate that the beneficial attributes of the present invention remain substantially undiminished even when the ratio of developer to dye base is substantially reduced. That is, the amount of developer used in Example 1C is only about one quarter of the amount of developer which is used in Example 1A. Despite this substantial reduction in developer, the result is observed to be substantially unchanged.

EXAMPLE 2A

The composition reported under column A in Table 2 is prepared. In particular, a liquid dye base comprising dye intermediate, carrier and sucrose is prepared in accordance with the composition indicated under the column heading AB in Table 4. The composition described in Table 4, column AB consists of about 0.5 parts by weight (PBW) of oxidative dyeing agent, about 95 PBW of carrier and about 4.5 PBW of sucrose. The carrier comprises about 15.7 PBW deionized water, about 11.7 PBW of isopropyl alcohol, about 15.5 PBW of alkalizer, about 29.7 PBW of detergent, about 13.5 PBW of thickening agent, about 9 PBW of spreading agent, about 0.6 PBW of anti-oxidant and about 0.2 PBW of chelating agent. The alkalizer consists of a 28 weight percent aqueous solution of ammonium hydroxide. The detergent consists of about 16.2 PBW of oleic acid (Emersal 6333LL) and about 13.5 PBW of Monoteric LMAB. The thickening agent consisted of about 13.5 PBW of laurel alcohol and the spreading agent consisted of about 9 PBW of the surfactant octylphenoxypoly(ethyleneoxy)ethanol (Igepal CA-630). The anti-oxidant consists of about 0.4 PBW of sodium sulphite and about 0.2 PBW of isoascorbic acid. The chelating agent consists of about 0.2 PBW of EDTA (Hamp-ene). The dye intermediate AB is described under the heading AB in Table 5.

A bleaching powder consisting of about 36 PBW of potassium persulfate, about 21 PBW of ammonium persulfate, about 36 PBW silica thickening agent, about 5 PBW of carboxymethylcellulose (CMC-7H3SF), about 1 PBW of fumed silica (CAB-O-SIL M5), and about 1 PBW of chelating agent (Hamp-ene acid) is prepared.

A developer (oxidizing agent) for the dye intermediate AB comprising a 6 percent by weight solution of hydrogen peroxide is provided. The developer thus comprised about 6 PBW of active coloring compound and about 94 PBW of carrier.

A coloring composition according to the present invention is prepared just prior to use by combining about 100 PBW of the dye base with about 30 PBW of the bleach booster powder and about 200 PBW of the developer. The coloring composition thus produced is described under column heading A in Table 2.

The coloring composition is applied to the hair of a human female subject having level two color hair by working it into a rich lather on the head of the female subject. After working the composition into the hair for about 3–5 minutes so as to ensure uniform application of the composition evenly to all of the hair of the subject, the composition is allowed to remain on the hair an additional 5–8 minutes. The hair of the subject is then rinsed thoroughly with water and allowed to dry. It is observed that the hair of the subject is altered from level two to level twelve blonde. Rich, deep tones are produced, and a brassy appearance is avoided. The hair is observed to be relatively undamaged by the treatment, and no irritation of the scalp of the subject or the skin of the hair professional is reported.

EXAMPLE 2B

Example 2A is repeated except that the final coloring composition is prepared just prior to use by combining about 100 PBW of the dye base with about 30 PBW of the bleaching powder and about 100 PBW of the developer. The coloring composition thus produced is described under column heading B in Table 2.

The coloring composition is applied to the hair of a human female subject having level two color hair by working it into a rich lather on the head of the female subject. After working the composition into the hair for about 3–5 minutes so as to ensure uniform application of the composition evenly to all of the hair of the subject, the composition is allowed to remain on the hair an additional 10–15 minutes. The hair of the subject is then rinsed thoroughly with water and allowed to dry. It is observed that the hair of the subject is altered from a level two to level twelve. Rich, deep tones are produced, and a brassy appearance is avoided. The hair is observed to be relatively undamaged by the treatment, and no irritation of the scalp of the subject or the skin of the hair professional is reported.

A comparison of Example 2A and 2B reveals that the beneficial attributes of the present invention remain substantially undiminished even when the ratio of developer to dye base is substantially reduced. That is, the amount of developer used in Example 2B is only about one half of the amount of developer used in Example 2A. Despite this substantial reduction in developer, the result is observed to be substantially unchanged.

EXAMPLE 2C

Example 2A is repeated except that the final coloring composition is prepared just prior to use by combining about 100 PBW of the dye base with about 30 PBW of the bleaching powder and about 50 PBW of the developer. The coloring composition thus produced is described under column heading C in Table 2.

The coloring composition is applied to the hair of a human female subject having level two color hair by working it into a rich lather on the head of the female subject. After working the composition into the hair for about 3–5 minutes so as to ensure uniform application of the composition evenly to all of the hair of the subject, the composition is allowed to remain on the hair an additional 5–8 minutes. The hair of the subject is then rinsed thoroughly with water and allowed to dry. It is observed that the hair of the subject is altered from a level two to level six. Rich, deep tones are produced, and a brassy appearance is avoided. The hair is observed to be relatively undamaged by the treatment, and no irritation of the scalp of the subject or the skin of the hair professional is reported.

A comparison of Examples 2A and 2C further illustrate that the beneficial attributes of the present invention remain substantially undiminished even when the ratio of developer to dye base is substantially reduced. That is, the amount of developer used in Example 2C is only about one quarter of the amount of developer which is used in Example 2A. Despite this substantial reduction in developer, the result is observed to be substantially unchanged.

EXAMPLE 3A

The composition reported under column A in Table 3 is prepared. In particular, a liquid dye base comprising dye intermediate, carrier and sucrose is prepared in accordance with the composition indicated under the column heading RF in Table 4. The composition described in Table 4, column RF consists of about 2.4 parts by weight (PBW) of oxidative dyeing agent, about 93.1 PBW of carrier and about 4.5 PBW of sucrose. The carrier comprises about 12.9 PBW deionized water, about 11.7 PBW of isopropyl alcohol, about 15.5 PBW of alkalizer, about 29.7 PBW of detergent, about 13.5 PBW of thickening agent, about 9 PBW of spreading agent, about 0.6 PBW of anti-oxidant and about 0.2 PBW of chelating agent. The alkalizer consists of a 28 weight percent aqueous solution of ammonium hydroxide. The detergent consists of about 16.2 PBW of oleic acid (Emersal 6333LL) and about 13.5 PBW of Monoteric LMAB. The thickening agent consists of about 13.5 PBW of lauryl alcohol and the spreading agent consists of about 9 PBW of the surfactant octylphenoxypoly(ethyleneoxy)ethanol (Igepal CA-630). The anti-oxidant consisted of about 0.4 PBW of sodium sulphite and about 0.2 PBW of isoascorbic acid. The chelating agent consisted of about 0.2 PBW of EDTA (Hamp-ene). The dyeing intermediate RF is described under the heading RF in Table 5.

A bleaching powder consisting of about 36 PBW of potassium persulfate, about 21 PBW of ammonium persulfate, about 36 PBW silica thickening agent, about 5 PBW of carboxymethylcellulose (CMC-7H3SF), about 1 PBW of fumed silica (CAB-O-SIL M5), and about 1 PBW of chelating agent (Hamp-ene acid) is prepared.

A developer (oxidizing agent) for the dye intermediate GB comprising a 6 percent by weight solution of hydrogen peroxide is provided. The developer thus comprises about 6 PBW of active coloring compound and about 94 PBW of carrier.

A coloring composition according to the present invention is prepared just prior to use by combining about 100 PBW of the first dye base with about 30 PBW of the bleaching powder and about 200PBW of the developer. The coloring composition thus produced is described under column heading A in Table 3.

The coloring composition is applied to the hair of a human female subject having level two brown color hair by working it into a rich lather on the head of the female subject. After working the composition into the hair for about 3–5 minutes so as to ensure uniform application of the composition evenly to all of the hair of the subject, the composition is allowed to remain on the hair an additional 5–8 minutes. The hair of the subject is then rinsed thoroughly with water and allowed to dry. It is observed that the hair of the subject is altered from a level two brown to a level twelve blond. Rich, deep tones are produced, and a brassy appearance is avoided. The hair is observed to be relatively undamaged by the treatment, and no irritation of the scalp of the subject or the skin of the hair professional is reported.

EXAMPLE 3B

Example 3A is repeated except that the final coloring composition is prepared just prior to use by Combining about 100 PBW of the dye base with about 30 PBW of the bleaching powder and about 100 PBW of the developer. The coloring composition thus produced is described under column heading B in Table 3.

The coloring composition is applied to the hair of a human female subject having level two color hair by working it into a rich lather on the head of the female subject. After working the composition into the hair for about 3–5 minutes so as to ensure uniform application of the composition evenly to all of the hair of the subject, the composition is allowed to remain on the hair an additional 10–15 minutes. The hair of the subject is then rinsed thoroughly with water and allowed to dry. It is observed that the hair of the subject is altered from a level two to level twelve. Rich, deep tones are produced, and a brassy appearance is avoided. The hair is observed to be relatively undamaged by the treatment, and no irritation of the scalp of the subject or the skin of the hair professional is reported.

A comparison of Examples 3A and 3B reveal that the beneficial attributes of the present invention remain substantially undiminished even when the ratio of developer to dye base is substantially reduced. That is, the amount of developer used in Example 3B is only about one half of the amount of developer which is used in Example 3A. Despite this substantial reduction in developer, the result is observed to be substantially unchanged.

EXAMPLE 3C

Example 1A is repeated except that the final coloring composition is prepared just prior to use by combining about 100 PBW of the dye base with about 30 PBW of the bleaching powder and about 50 PBW of the developer. The coloring composition thus produced is described under column heading C in Table 3.

The coloring composition is applied to the hair of a human female subject having level two color hair by working it into a rich lather on the head of the female subject. After working the composition into the hair for about 3–5 minutes so as to ensure uniform application of the composition evenly to all of the hair of the subject, the composition is allowed to remain on the hair an additional 5–8 minutes. The hair of the subject is then rinsed thoroughly with water and allowed to dry. It is observed that the hair of the subject is altered from a level two to level six. Rich, deep tones are produced, and a brassy appearance is avoided. The hair is observed to be relatively undamaged by the treatment, and no irritation of the scalp of the subject or the skin of the hair professional is reported.

A comparison of Examples 3A and 3C further illustrate that the beneficial attributes of the present invention remain substantially undiminished even when the ratio of developer to dye base is substantially reduced. That is, the amount of developer used in Example 3C is only about one quarter of the amount of developer which is used in Example 3A. Despite this substantial reduction in developer, the result is observed to be substantially unchanged.

EXAMPLE 4

The bleaching composition reported under column B in Table 6 is prepared. In particular, a liquid bleach oil comprising carrier and sucrose is prepared in accordance with the composition indicated in Table 7. The composition described in Table 7 consists of about 95 PBW of carrier and about 5 PBW of sucrose.

A bleach booster powder consisting of about 36 PBW of potassium persulfate, about 21 PBW of ammonium persulfate, about 36 PBW silica thickening agent, about 5 PBW of carboxymethylcellulose (CMC-7H3SF), about 1 PBW of fumed silica (CAB-O-SIL M5), and about 1 PBW of chelating agent (Hamp-ene acid) is prepared.

A 6 percent by weight solution (20 vol) of hydrogen peroxide is provided. The solution thus comprises about 6

PBW of active coloring compound (oxidizing agent) and about 94 PBW of carrier.

A coloring composition according to the present invention is prepared just prior to use by combining about 30 PBW of the bleach oil with about 24 PBW of the bleach booster powder and about 30 PBW of the peroxide solution. The coloring composition thus produced is described under column heading B in Table 6.

The coloring composition is applied to the hair of a human female subject having level three color hair by working it into a rich lather on the head of the female subject. After working the composition into the hair for about 3–5 minutes so as to ensure uniform application of the composition evenly to all of the hair of the subject, the composition is allowed to remain on the hair an additional 10 minutes with the application of heat. The hair of the subject is then rinsed thoroughly with water and allowed to dry. It is observed that the hair of the subject is altered from a level three to a level twelve pale yellow blonde. Rich, deep tones are produced, and a brassy appearance is avoided. The hair is observed to be relatively undamaged by the treatment, and no irritation of the scalp of the subject or the skin of the hair professional is reported.

COMPARATIVE EXAMPLE 1

The bleaching procedures used in Example 4 are repeated using the materials provided with a first commercially available hair bleaching product.

Two (2) ounces of the bleach oil and 48 grams of the powder provided with the product are combined with 4 ounces of 6 wt. % hydrogen peroxide solution.

The coloring composition is applied to the hair of a human female subject having level three color hair by working it into a rich lather on the head of the female subject. After working the composition into the hair for about 3–5 minutes so as to ensure uniform application of the composition evenly to all of the hair of the subject, the composition is allowed to remain on the hair an additional 10 minutes with the application of heat. The hair of the subject is then rinsed thoroughly with water and allowed to dry. It is observed that the hair of the subject is altered from a level three to a level eight gold with an unattractive red-orange tone.

COMPARATIVE EXAMPLE 2

The bleaching procedures used in Example 4 are repeated using the materials provided with a second commercially available hair bleaching product.

Two (2) ounces of the bleach oil and 48 grams of the powder provided with the product are combined with 4 ounces of 6 wt. % hydrogen peroxide solution.

The coloring composition is applied to the hair of a human female subject having level three color hair by working it into a rich lather on the head of the female subject. After working the composition into the hair for about 3–5 minutes so as to ensure uniform application of the composition evenly to all of the hair of the subject, the composition is allowed to remain on the hair an additional 10 minutes with the application of heat. The hair of the subject is then rinsed thoroughly with water and allowed to dry. It is observed that the hair of the subject is altered from a level three to a level nine gold with a slight reddish edge.

COMPARATIVE EXAMPLE 3

A non-oxidative bleaching procedure using the materials provided with a third commercially available hair coloring product.

The materials are applied, according to the instructions provided, to the hair of a human female subject having level three color hair. It is observed that the hair of the subject is altered to a level ten light yellow with unattractive slight pale orange.

EXAMPLE 5

The coloring composition reported under column GB in Table 6 is prepared. In particular, a liquid bleach oil comprising carrier and sucrose is prepared in accordance with the composition indicated in Table 7; a liquid dye base comprising dye intermediate, carrier and sucrose is prepared in accordance with the composition indicated under the column heading GB in Table 4; and a bleach booster powder consisting of about 36 PBW of potassium persulfate, about 21 PBW of ammonium persulfate, about 36 PBW silica thickening agent, about 5 PBW of carboxymethylcellulose (CMC-7H3SF), about 1 PBW of fumed silica (CAB-O-SIL M5), and about 1 PBW of chelating agent (Hamp-ene acid) is prepared.

A 6 percent by weight solution (20 vol) of hydrogen peroxide is provided. The solution thus comprised about 6 PBW of active coloring compound (oxidizing agent) and about 94 PBW of carrier.

A coloring composition according to the present invention is prepared just prior to use by combining about 30 PBW of the bleach oil, about 30 PBW of dye base, about 24 PBW of the bleach booster powder and about 30 PBW of the peroxide solution. The coloring composition thus produced is described under column heading GB in Table 6.

The coloring composition is applied to the hair of a human female subject having level three color hair by working it into a rich lather on the head of the female subject. After working the composition into the hair for about 3–5 minutes so as to ensure uniform application of the composition evenly to all of the hair of the subject, the composition is allowed to remain on the hair an additional 10 minutes with the application of heat. The hair of the subject is then rinsed thoroughly with water and allowed to dry. It is observed that the hair of the subject is altered from a level three to a level ten pale golden blonde. Rich, deep tones are produced, and a brassy appearance is avoided. The hair is observed to be relatively undamaged by the treatment, and no irritation of the scalp of the subject or the skin of the hair professional is reported.

COMPARATIVE EXAMPLE 4

The bleaching procedures used in Comparative Example 1 are repeated, except 1 ounce of the lightest Golden Blonde dyeing materials provided with the product are added to the composition prior to application to the hair.

It is observed that the hair of the subject is altered from a level three to a level six orange with an unattractive red-orange tone.

COMPARATIVE EXAMPLE 5

The bleaching procedures used in Comparative Example 2 are repeated, except one ounce of the lightest Golden Blonde dyeing materials provided with the product are added to the composition prior to application to the hair.

It is observed that the hair of the subject is altered from a level three to a level seven light gold with unattractive orange brassiness.

EXAMPLE 6

The coloring composition reported under column AB in Table 6 is prepared. In particular, a liquid bleach oil comprising carrier and sucrose is prepared in accordance with the composition indicated in Table 7; a liquid dye base comprising dye intermediate, carrier and sucrose is prepared in accordance with the composition indicated under the column heading AB in Table 4; and a bleach booster powder consisting of about 36 PBW of potassium persulfate, about 21 PBW of ammonium persulfate, about 36 PBW silica thickening agent, about 5 PBW of carboxymethylcellulose (CMC-7H3SF), about 1 PBW of fumed silica (CAB-O-SIL MS), and about 1 PBW of chelating agent (Hamp-ene acid) is prepared.

A 6 percent by weight solution (20 vol) of hydrogen peroxide is provided. The solution thus comprised about 6 PBW of active coloring compound (oxidizing agent) and about 94 PBW of carrier.

A coloring composition according to the present invention is prepared just prior to use by combining about 30 PBW of the bleach oil, about 30 PBW of dye base, about 24 PBW of the bleach booster powder and about 30 PBW of the peroxide solution. The coloring composition thus produced is described under column heading AB in Table 6.

The coloring composition is applied to the hair of a human female subject having level three color hair by working it into a rich lather on the head of the female subject. After working the composition into the hair for about 3–5 minutes so as to ensure uniform application of the composition evenly to all of the hair of the subject, the composition is allowed to remain on the hair an additional 10 minutes with the application of heat. The hair of the subject is then rinsed thoroughly with water and allowed to dry. It is observed that the hair of the subject is altered from a level three to a level twelve pale beige slight ash blonde. Rich, deep tones are produced, and a brassy appearance is avoided. The hair is observed to be relatively undamaged by the treatment, and no irritation of the scalp of the subject or the skin of the hair professional is reported.

COMPARATIVE EXAMPLE 6

The bleaching procedures used in Comparative Example 2 are repeated, except i ounce of the lightest Ash Blonde dyeing materials provided with the product supplied are added to the composition prior to application to the hair.

It is observed that the hair of the subject is altered from a level three to a level seven gold with an unattractive deep red-orange brassiness.

COMPARATIVE EXAMPLE 7

The bleaching procedures used in Comparative Example 2 are repeated, except one ounce of the lightest Ash Blonde dyeing materials provided with the product are added to the composition prior to application to the hair.

It is observed that the hair of the subject is altered from a level three to a level seven-eight gold with an unattractive red-gold brassiness.

EXAMPLE 7

The coloring composition reported under column RF in Table 6 is prepared. In particular, a liquid dye oil comprising carrier and sucrose is prepared in accordance with the composition indicated in Table 7; a liquid dye base comprising dye intermediate, carrier and sucrose is prepared in accordance with the composition indicated under the column heading RF in Table 4; and a bleach booster powder consisting of about 36 PBW of potassium persulfate, about 21 PBW of ammonium persulfate, about 36 PBW silica thickening agent, about 5 PBW of carboxymethylcellulose (CMC-7H3SF), about 1 PBW of fumed silica (CAB-O-SIL M5), and about 1 PBW of chelating agent (Hamp-ene acid) is prepared.

A 6 percent by weight solution (20 vol) of hydrogen peroxide is provided. The solution thus comprised about 6 PBW of active coloring compound (oxidizing agent) and about 94 PBW of carrier.

A coloring composition according to the present invention is prepared just prior to use by combining about 30 PBW of the bleach oil, about 30 PBW of dye base, about 24 PBW of the bleach booster powder and about 30 PBW of the peroxide solution. The coloring composition thus produced is described under column heading RF in Table 6.

The coloring composition is applied to the hair of a human female subject having level three color hair by working it into a rich lather on the head of the female subject. After working the composition into the hair for about 3–5 minutes so as to ensure uniform application of the composition evenly to all of the hair of the subject, the composition is allowed to remain on the hair an additional 10 minutes with the application of heat. The hair of the subject is then rinsed thoroughly with water and allowed to dry. It is observed that the hair of the subject is altered from a level three to a level nine-ten light true red. Rich, deep tones are produced, and a brassy appearance is avoided. The hair is observed to be relatively undamaged by the treatment, and no irritation of the scalp of the subject or the skin of the hair professional is reported.

COMPARATIVE EXAMPLE 8

The bleaching procedures used in Comparative Example 3 are repeated, except 1 ounce of the RED dyeing materials provided with the product are added to the composition prior to application to the hair.

It is observed that the hair of the subject is altered from a level three to an unattractive level five burnt orange.

COMPARATIVE EXAMPLE 9

The bleaching procedures used in Comparative Example 3 are repeated, except one ounce of the Red dyeing materials provided with the product are added to the composition prior to application to the hair.

It is observed that the hair of the subject is altered from a level three to an unattractive level six yellow red with orange brassiness.

TABLE 1

GOLDEN BLONDE COLORING COMPOSITIONS

| | Concentration, Wt % | | |
|---|---|---|---|
| Component | A | B | C |
| Oxidizing Agent | | | |
| $K_2S_2O_8$ | 3.3 | 4.7 | 6.1 |
| $(NH_4)_2S_2O_8$ | 1.8 | 2.6 | 3.3 |
| $H_2O_2$ | 3.6 | 2.6 | 1.7 |
| Carrier | | | |
| $H_2O$ | 61.3 | 47.5 | 34.4 |
| Isopropyl Alcohol | 3.6 | 5.1 | 6.5 |
| Alkalizer | 4.8 | 6.9 | 8.8 |
| Detergent | 9.1 | 13 | 16.6 |
| Spreading Agent | 2.7 | 3.9 | 5 |
| Anti-oxidant | 0.2 | 0.3 | 0.3 |
| Chelating Agent | 0.2 | 0.2 | 0.3 |
| Thickener | 7.8 | 11.1 | 14.3 |
| Flow Agent | 0.1 | 0.1 | 0.1 |
| Dye Intermediate GB | 0.1 | 0.1 | 0.1 |
| Sucrose | 1.4 | 1.9 | 2.5 |
| | 100.0 | 100.0 | 100.0 |
| Ratio | | | |
| Sucrose:Active Coloring Compound | 0.22:1 | 0.19:1 | 0.16:1 |

TABLE 2

ASH BLONDE COLORING COMPOSITIONS

| | Concentration, Wt % | | |
|---|---|---|---|
| Component | A | B | C |
| Oxidizing Agent | | | |
| $K_2S_2O_8$ | 3.3 | 4.7 | 6.1 |
| $(NH_4)_2S_2O_8$ | 1.8 | 2.6 | 3.3 |
| $H_2O_2$ | 3.6 | 2.6 | 1.7 |
| Carrier | | | |
| $H_2O$ | 61.4 | 47.5 | 34.2 |
| Isopropyl Alcohol | 3.6 | 5.1 | 6.5 |
| Alkalizer | 4.7 | 6.8 | 8.6 |
| Detergent | 9.0 | 12.9 | 16.5 |
| Spreading Agent | 2.7 | 3.9 | 5 |
| Anti-oxidant | 0.2 | 0.3 | 0.3 |
| Chelating Agent | 0.2 | 0.2 | 0.3 |
| Thickener | 7.8 | 11.2 | 14.3 |
| Flow Agent | 0.1 | 0.1 | 0.2 |
| Dye Intermediate AB | 0.2 | 0.2 | 0.3 |
| Sucrose | 1.4 | 2.0 | 2.5 |
| | 100.0 | 100.0 | 100.0 |
| Ratio | | | |
| Sucrose:Active Coloring Compound | 0.22:1 | 0.19:1 | 0.16:1 |

TABLE 3

RED FLAME COLORING COMPOSITIONS

| | Concentration, Wt % | | |
|---|---|---|---|
| Component | A | B | C |
| Oxidizing Agent | | | |
| $K_2S_2O_8$ | 3.3 | 4.7 | 6.1 |
| $(NH_4)_2S_2O_8$ | 1.8 | 2.6 | 3.3 |
| $H_2O_2$ | 3.6 | 2.6 | 1.7 |
| Carrier | | | |
| $H_2O$ | 61.0 | 46.5 | 33.4 |
| Isopropyl Alcohol | 3.5 | 5.1 | 6.5 |
| Alkalizer | 4.7 | 6.7 | 8.6 |
| Detergent | 19.0 | 12.9 | 16.5 |
| Spreading Agent | 2.7 | 3.9 | 5 |
| Anti-oxidant | 0.2 | 0.3 | 0.3 |
| Chelating Agent | 0.2 | 0.2 | 0.3 |
| Thickener | 7.8 | 11.3 | 14.3 |
| Flow Agent | 0.1 | 0.1 | 0.2 |
| Dye Intermediate RF | 0.7 | 1.0 | 1.3 |
| Sucrose | 1.4 | 2.0 | 2.5 |
| | 100.0 | 100.0 | 100.0 |
| Weight Ratio | | | |
| Sucrose:Active Coloring Compound | 0.2:1 | 0.18:1 | 0.15:1 |

TABLE 4

DYE BASES

| | Concentration, Wt % | | |
|---|---|---|---|
| Component | GB | AB | RF |
| Dye Intermediate GB | 0.2 | — | — |
| Dye Intermediate AB | — | 0.5 | — |
| Dye Intermediate RF | — | — | 2.4 |
| Carrier | | | |
| Deionized Water | 15.7 | 14.8 | 12.9 |
| Isopropyl Alcohol | 11.7 | 11.7 | 11.7 |
| $NH_4OH$ (28% aq. sol) | 15.5 | 15.5 | 15.5 |
| Oleic Acid | 16.2 | 16.2 | 16.2 |
| Lauramido Propyl Betaine | 13.5 | 13.5 | 13.5 |
| Lauryl Alcohol | 13.5 | 13.5 | 13.5 |
| Octylphenoxypoly (ethyleneoxy)ethanol | 9 | 9 | 9 |
| $NaSO_4$ | 0.4 | 0.4 | 0.4 |
| Isoascorbic Acid | 0.2 | 0.2 | 0.2 |
| EDTA | 0.2 | 0.2 | 0.2 |
| Sucrose | 4.5 | 4.5 | 4.5 |
| | 100.0 | 100.0 | 100.0 |

TABLE 5

DYE INTERMEDIATES

| | Concentrations, PBW | | |
|---|---|---|---|
| Component | GB | AB | RF |
| p-phenylenediamine | — | 21 | — |
| 2,4,-diaminophenetol $SO_4$ | — | 16 | — |
| p-nitro-o-phenylenediamine | 23 | 28 | 100 |
| m-Aminophenol | — | 19 | — |
| o-Aminophenol | — | 20 | — |
| Resorcinol | — | 160 | 120 |
| 5-nitro-2-aminophenol | — | 52 | — |
| p-Aminophenol | 60 | 28 | 80 |
| o-nitro-p-phenylenediamine | 20 | — | 40 |
| H.C. -Yellow #5 | 22 | — | — |
| 5-amino-2-methyl phenol | 60 | — | 900 |
| 4-chlororesorcinol | — | — | 120 |

TABLE 6

COLORING COMPOSITIONS

| Component | Concentration, Wt % | | | |
|---|---|---|---|---|
| | B | GB | AB | RF |
| Oxidizing Agent | | | | |
| $K_2S_2O_8$ | 10.4 | 7.7 | 7.7 | 7.7 |
| $(NH_4)_2S_2O_8$ | 6.1 | 4.4 | 4.4 | 4.5 |
| $H_2O_2$ | 2.1 | 1.6 | 1.6 | 1.6 |
| Carrier | | | | |
| $H_2O$ | 38.3 | 32.2 | 32.2 | 31.7 |
| Isopropyl Alcohol | 4.6 | 6.5 | 6.5 | 6.5 |
| Alkalizer | 3.6 | 6.7 | 6.7 | 6.7 |
| Detergent | 11.7 | 16.5 | 16.5 | 16.5 |
| Spreading Agent | 3.6 | 5.0 | 5.0 | 5.0 |
| Anti-oxidant | — | 0.2 | 0.2 | 0.2 |
| Chelating Agent | 0.3 | 0.2 | 0.2 | 0.2 |
| Thickener | 17.2 | 16.2 | 16.2 | 16.2 |
| Flow Agent | 0.3 | 0.2 | 0.2 | 0.2 |
| Dye Intermediate | — | 0.1 | 0.1 | 0.6 |
| Sucrose | 1.8 | 2.5 | 2.5 | 2.5 |
| | 100.0 | 100.0 | 100.0 | 100.0 |
| Weight Ratio | | | | |
| Sucrose:Active Coloring Compound | 0.1:1 | 0.18:1 | 0.17:1 | 0.17:1 |

TABLE 7

BLEACH OIL

| Component | Concentration, Wt % A |
|---|---|
| Oxidizing Agent | |
| $K_2S_2O_8$ | — |
| $(NH_4)_2S_2O_8$ | — |
| $H_2O_2$ | — |
| Carrier | |
| $H_2O$ | 14 |
| Isopropyl Alcohol | 13 |
| Alkalizer (28%$NH_4OH$) | 10 |
| Oleic Acid | 18 |
| Lauramido Propyl Betaine | 15 |
| Lauryl Alcohol | 15 |
| Octylphenoxypoly(ethyleneoxy)ethanol | 10 |
| Dye Intermediate | — |
| Sucrose | 5 |
| | 100 |

What is claimed is:

1. A composition for achieving a predetermined alteration of hair color in vivo comprising:
   (a) from about 85 to about 99 percent by weight of a coloring agent consisting essentially of (i) an oxidative dyeing agent, (ii) a first oxidizing agent comprising a salt of persulfuric acid and a second oxidizing agent comprising hydrogen peroxide and (iii) a carrier for said oxidative dyeing agent and oxidizing agents, said oxidative dyeing agent being present in an amount effective to obtain the predetermined alteration of hair color, the amount of said first oxidizing agent being effective to remove color from the hair and the amount of said second oxidizing agent being sufficient to develop said oxidative dyeing agent, said carrier being present in an amount of about 40 to about 65% by wt. of the composition and consisting essentially of a mixture of water and an alcohol, a thickening agent in an amount of 5 to 15 percent by weight of the composition and an alkalizer; and
   (b) sucrose, the weight ratio of said sucrose to said agents (i) and (ii) being from about 0.1:1 to about 1:1.

2. The composition according to claim 1 wherein said oxidative dyeing agent is selected from the group consisting of substituted phenols, diamines, and mixtures of these.

3. The composition according to claim 2 wherein said oxidative dyeing agent comprises amino substituted phenol.

4. The composition of claim 1 wherein said first and second oxidizing agents together comprise from about 3 to about 20 percent by weight of said composition.

5. The composition of claim 4 wherein said first and second oxidizing agents together comprise from about 8 to about 14 percent by weight of said composition.

6. The composition of claim 5 wherein said first and second oxidizing agents together comprise from about 8 to about 11 percent by weight of said composition.

7. The composition of claim 1 wherein the weight ratio of said sucrose to said agents is from about 0.2:1 to about 0.4:1.

8. A composition for alteration of hair color consisting essentially of:
   (a) from about 85 to about 99 percent by weight of a color removing agent consisting essentially of (i) an oxidizing bleaching agent in an amount effective to remove color from the hair (ii) an oxidizing agent in an amount effective to activate said oxidizing bleaching agent and (iii) a carrier for said color removing agent said carrier consisting essentially of water, alcohol and a thickening agent in an amount of about 5–15% by weight of the composition; and
   (b) sucrose, the weight ratio of said sucrose to said agents (i) and (ii) being from about 0.1:1 to about 1:1.

9. The composition of claim 8 wherein the weight ratio of said sucrose to said agents is from about 0.1: 1 to about 0.3:1.

10. The composition of claim 8 wherein said oxidizing bleaching agent comprises from about 10 to about 20 percent by weight of said composition.

* * * * *